US00RE34424E

United States Patent [19]

Walman

[11] E Patent Number: Re. 34,424

[45] Reissued Date of Patent: Oct. 26, 1993

[54] INTRAOCULAR LENS

[76] Inventor: Gerald B. Walman, 10615 W. Thunderbird Blvd. #D200, Sun City, Ariz. 85351

[21] Appl. No.: 863,966

[22] Filed: May 16, 1986

Related U.S. Patent Documents

Reissue of:

[64] Patent No.: 4,504,981
Issued: Mar. 19, 1985
Appl. No.: 306,326
Filed: Sep. 28, 1981

[51] Int. Cl.[5] ..... A61F 2/16
[52] U.S. Cl. ..... 623/6
[58] Field of Search ..... 623/6

[56] References Cited

U.S. PATENT DOCUMENTS

| | | | |
|---|---|---|---|
| 4,174,543 | 11/1979 | Kelman | 623/6 |
| 4,249,271 | 2/1981 | Poler | 623/6 |
| 4,261,065 | 4/1981 | Tennant | 623/6 |
| 4,370,760 | 2/1983 | Kelman | 623/6 |
| 4,403,353 | 9/1983 | Tennant | 623/6 |

OTHER PUBLICATIONS

The Lindstrom Centrex Style 20 Posterior Chamber Lens, Advertisement Brochure, Surgiden Corp., 1421 State Street, Santa Barbara, CA 93101, Jan. 4, 1981, (4 pages).

*Primary Examiner*—Randall L. Green
*Assistant Examiner*—Mary Beth O. Jones
*Attorney, Agent, or Firm*—Cahill Sutton & Thomas

[57] ABSTRACT

The intraocular lens, whether for implantation in the anterior or posterior chamber of the eye, embodies laterally extending non-radially oriented supporting loops which accommodate by bending compressive forces imposed thereon without flexing or bowing of the lens. The anterior chamber intraocular lens implants are fixated in the angle of the anterior chamber and locate the lens anterior of and in noncontacting relationship with the iris whether extracapsular or intracapsular surgery has been performed. The posterior chamber intraocular lens implants may be fixated in the groove posterior to the iris in an extracapsular eye or in the anterior chamber after penetration of the supporting loop segments through peripheral openings in the iris in an intracapsular eye, with either location in fixation, the lens anatomically replaces the surgically removed lens of the eye.

86 Claims, 12 Drawing Sheets

INTRAOCULAR LENS

Matter enclosed in heavy brackets [ ] appears in the original patent but forms no part of this reissue specification; matter printed in italics indicates the additions made by reissue.

The present invention relates to intraocular lenses and, more particularly, to lenses having stable fixation members providing superior flexibility to minimize irritation of tissues and reduce postoperative complications.

The visual rehabilitation of a patient afflicted with cataract has been a controversial topic within the cognoscente for decades. To understand the concept of intraocular lens implants, one must first have an intimate knowledge of the anatomy of the eye and the characteristics of a cataract. Referring to a cross-sectional diagram of an eye, light enters through the cornea. The cornea is a clear transparent tissue that serves as a window which allows entry of light and provides some amount of focusing capability. The light transverses the anterior chamber and penetrates the crystaline lens. The lens acts as a major focusing element for the light. The light, after being focused by the lens, continues on its path through the vitreous and impinges upon the retina. The impinging light is transformed into electrical impulses by the reaction of layers of complex specialized retinal nerves. The nerves transmit the electrical impulses to the brain which translates them into visual sensations.

The word "cataract" refers to a clouding of the normally clear lens. The causes of cataract need not be reviewed except to say that senile cataract is an extremely common afflication of patients over the age of sixty and leads to varying amounts of significant visual disability. When a cataract is present, the light normally penetrating the crystaline lens for focusing is impaired by the clouded areas. When the cataract becomes severe enough, the only treatment available is surgical removal of the cataract which is equivalent to surgical removal of the crystaline lens. At the present time, there are no medicinal cures for most patients afflicted with cataract.

Innumerable techniques for cataract removal have been described and are currently in practice. The techniques for cataract removal fall into one of two broad categories: (1) intracapsular cataract surgery involves removal of the entire cataract or crystaline lens together with its supporting capsular tissue. Removal is usually accomplished surgically with the aid of cryosurgery and the resulting eye is left with the vitreous cavity in intimate contact with the posterior surface of the iris. (2) extracapsular cataract surgery involves the removal of the cataract or crystaline lens interior while leaving the capsular tissue either partially or entirely intact within the eye. The important distinction between these two categories is that in extracapsular surgery the capsular tissue or outer envelope of the lens is left in place to separate part or all of the vitreous from the more anterior structures of the eye.

With the surgical removal of the crystaline lens, the resulting eye is deficient in focusing power. In the early years of cataract surgery, this deficiency of focusing power was corrected by using a thick lens held in front of the eye by a spectacle frame. This thick lens did correct the focusing power in the central parts of a patient's field of view but was very poor in focusing upon objects that were offcenter and toward the periphery. As a result, the patients wearing these thick lenses had a type of tunnel vision; any objects that were not in the center vision were very much distorted or completely absent from view. Because the lenses were very thick, the spectacles were very difficult to fit properly, were constantly in need of adjustment and the cosmetic effect of the lens were very poor.

Improvements in visual rehabilitation came with the availability of contact lenses. A contact lens is located on the surface of the cornea and compensates for the deficiency in focusing power. With the contact lens in place, the patient does not have the difficulties of tunnel vision, the peripheral vision is very much improved and the distortion attendant the thick lens is absent. The difficulties and detriments attendant contact lenses are well known. In example, many people cannot tolerate the feel or sensation of a contact lens on their eye; lens hygiene is a constant problem and the patient must be meticulous about constant cleaning; contact lenses are easily lost. The most significant drawback of contact lenses is the fact that a patient with a cataract is very often a patient in advanced years who does not have the manual dexterity for proper handling of the contact lens.

A third alternative of visual rehabilitation is the use of an intraocular lens implant (IOL). An IOL is a small piece of manufactured plastic that is inserted into the eye at surgery. The difficulties enumerated above attendant thick lenses and contact lenses are completely eliminated. Moreover, the patient has no sensation of the presence of the IOL and if the implant is successful, the IOL is in the eye permanently to replace the lost focusing power of the removed crystaline lens.

An intraocular lens falls into one of three broad categories depending upon its position within the eye. An anterior chamber untraocular lens is placed within the anterior chamber in front of the iris. Its fixation is dependent on various styles of loops that are supported in the angles of the anterior chamber, whereby the iris tissue is allowed to move freely. From a technical standpoint, the anterior chamber IOL's are the easiest to implant. The difficulties with prior art anterior chamber IOL's include: (1) deficient manufacturing methods which leave rough edges of the implant and result in chronic irritation (iritis), elevated intraocular pressure (glaucoma) and bleeding within the anterior chamber (hyphema); (2) the lens support structure is of solid plastic construction, rather than flexible loop construction, which can lead to blockage of the normal aqueous flow within the eye (pupillary block glaucoma); (3) the lack of sufficient flexibility of the support structure leads to difficulties with tenderness on touching of the eye and normal movements during one's daily activities can lead to chronic irritation whithin the eye; (4) the prior art anterior chamber IOL's have to be matched in size to the patient's eye which increases IOL inventory problems. More importantly, without accurate measurements of the patient's eyes, an inflexible or insufficiently flexible IOL that is too small results in increased movement of the implant that can lead to chronic irritation while an implant that is too large tends to distort the eye, cause discomfort and lead to chronic irritation. The major advantage of an anterior chamber IOL is that it may be used after either intracapsular or extracapsular surgery.

An iris supported IOL is an implant that depends on iris tissue or a combination of iris tissue and capsular tissue for its support. It has significant disadvantages because of its lack of uniplanar design, and its constant iris contact. As the present invention is not an iris supported IOL, further discussion of the prior art pertinent to iris supported IOL's need not be undertaken.

A posterior chamber IOL is inserted behind the iris to position the lens in the exact anatomical position of the previously removed cataract or crystaline lens. The major disadvantage of prior art posterior chamber IOL's is that the cataract must be removed by extracapsular techniques. The advantages attendant posterior chamber IOL's in general include: (1) fixation at the posterior capsule provides good stability to the eye; (2) as no iris fixation is present, the pupil behaves normally; (3) the implant is uniplanar and therefore is generally easy to insert without damaging other structures; (4) dislocation is rare but if it should occur, the implant does not dislocate anteriorly to damage the cornea; and (5) the patient is visually rehabilitated as nearly as is physiologically possible since the implant is in the exact location as the previously removed crystaline lens.

Historically, the earliest posterior chamber IOL implants were performed by Harold Ridley in the late 1940's. The Ridley biconvex lens was about the same shape as, but had approximately 1 mm smaller diameter than, the normal human lens. Its weight in air was 112 mg, an extremely heavy weight for an object to be implanted in the eye. The weight and relatively large diameter caused the Ridley lens to exert undue pressure on the ciliary body, the annular structure on the inner surface of the eye surrounding the lens and including the ciliary muscle and the ciliary process to which the zonules are connected. Other adverse side effects occurred: glaucoma was noted; in some instances, the lens became loose and fell into the back of the eye; and, many cases of downward decentration were noted, wherein the lens shifted downwardly so that its axis was no longer centered with respect to the pupil. For all of these reasons, the Ridley IOL soon was abandoned.

A related IOL designed by Stampelli for use in the anterior chamber was tried in the early 1950's. This IOL seated in the angle of the eye, where the cornea and iris are joined. Because of poor peripheral design, the use of such IOL's often caused destruction of the endothelium, a very thin layer of live cells on the interior of the cornea. This is very serious complication, and use of this form of anglefixated anterior chamber IOL soon was stopped.

Other attempts have been made to accomplish the objective of fixation without suturing. The Choyce Mark VIII anterior chamber IOL is a thin, generally flat unitary structure having the appearance, when viewed frontally, of an elongated rectangle with rounded corners and notched ends. The rounded corners seat in the angle and center the planoconvex or biconvex optical portion in front of the pupil. The IOL is easy to implant and thus as gained acceptance by many surgeons However, cases of CME have been noted with these IOL's. Also, because of inflexibility tension is placed on the angle, resulting in tenderness and irritability to the eye, particularly when rubbed.

Another form of self-centering IOL was developed by Barraquer, initially for anterior chamber use and later adapted for placement in the posterior chamber. This IOL includes a pair of hook-shaped flexible loops extending from opposite sides of the optical portion. Since one end of each loop is free, the loops would flex sufficiently to snap in place. When installed in the anterior chamber, the hooks seated in the angle.

Shearing adapted the Barraquer design for use in the posterior chamber. With extracapsular extraction, the hooks may be implaced within the cleft of the capsule. However, during implantation the hooks are held under tension, and when released may fly up behind the iris and seat directly against the ciliary body. Alternatively, with extracapsular extraction, the hooks may intentionally be installed against the ciliary body. A disadvantage of such an implant is that the hooks continuously exert tension on the ciliary body. An increase in the occurrence of retinal detachments has been noted amongst patients having such Shearing or Barraquer posterior chamber IOL's. It is likely that the retinal detachments are associated with the tension exerted on the side of the eye in the vicinity of the ciliary sulcus. Furthermore, tenderness also is noted with such an IOL when the eye is rubbed.

A further form of posterior chamber of IOL was developed by Pearce. This IOL generally resembles a three-bladed airplane propeller, the blades of which are inserted into the fornix of the capsule after extracapsular extraction. The disadvantage of the IOL is that it is of fixed size and therefore the surgeon must take several different sizes into the operating room; if the first does not fit, he must remove it from the eye and insert another of smaller or larger size. It is also recommended to be sutured for centration. The surgical procedure itself is made unnecessarily complex.

Still another form of prior art IOL that is advantageously used with extracapsular surgery is the Binkhorst iridocapsular lens. This is a variant of Binkhorst's iris clip lens, but it does not have anterior loops. The optical portion itself is centered in the pupil with the rim of the lens lightly touching the front of the iris. The single pair of loops, bent slightly rearward, lie behind the lens and are buried in the iridocapsular cleft. After the surgery, the capsule fibroses or develops iridocapsular adhesions which embed part of the posterior loops, thereby giving extra stability to the implanted lens.

Various United States patents directed to various types of IOL's include the following. U.S. Pat. Nos. 3,906,551 and 3,971,073 illustrate examples of iris supported lenses. U.S. Pat. No. 4,079,470 describes an iris supported IOL and is particularly directed to the material of lenses and coatings therefor. U.S. Pat. No. 4,077,071 is directed to increasing the bouyancy of an IOL implant. U.S. Pat. No. 4,170,043 is also primarily directed to coatings for IOL implants. U.S. Pat. No. 4,168,547 is related primarily to materials for IOL implants. U.S. Pat. No. 4,110,848 is directed to an only slightly flexible posterior chamber IOL implant which must be used in an extracapsular eye. U.S. Pat. No. 4,244,060 describes a posterior chamber IOL implant which employs numerous filaments for supporting the implant. U.S. Pat. No. 4,092,743 is directed to a posterior chamber IOL implant of solid loop material which has no flexibility and the implant can only be used in an extracapsular eye. A variant of the invention, an anterior chamber IOL implant is depicted in FIG. 7 and illustrates an implant presently in production and in use. Either of the types of implants described depend upon three point fixation which method of fixation has been severely critized in the scientific literature because of an often resulting tilting of the lens. Moreover, with three point fixation, one of the ends of the implant can work its way through a peripheral iridectomy and lead to a very unstable lens having only a two point fixation. Little flexibility is available from the implants described and the problems resulting therefrom and enumerated above occur. U.S. Pat. No. 4,174,543 describes an anterior chamber IOL implant, which implant is intended to have flexible support members. However, the configuration and orientation of the support members either preclude flexibility in response to forces exerted radially inwardly within certain angular orientations or within certain relatively significant arcs, depending upon the configuration under examination. The limitations of flexibility of the support members and the resulting lack of compressibility of the proximal segments is a severe limitation on the size of the eye in which any given IOL may be implanted.

The intraocular lens implants embodied by the present invention, whether for implantation in the anterior or posterior chamber, incorporate supporting legs or loops of one or more segments At least a segment of each loop is curved and none of the segments of any loop is coincident with a radial of the lens. Thereby, any compressive force exerted radially by the eye upon a point along opposed supporting loops will be accommodated by a bending of one or more segments of each supporting loop. The anterior chamber intraocular lenses may be used after either intracapsular or extracapsular surgery and the points of fixation of the supporting loops are supported in the angle of the anterior chamber. The posterior chamber intraocular lenses are inserted posterior to the iris in the exact anatomical position of the previously removed cataract, which cataract may be removed by either intracapsular or extracapsular surgery. The points of fixation of the supporting loops are entirely posterior to the iris and anterior to the remaining lens capsule in an extracapsular eye. In an intracapsular eye, at least one of the supporting loops is maneuvered from the posterior chamber to the anterior chamber through a peripheral opening of the iris and fixated in the peripheral portion of the anterior chamber. Manipulation holes or grooves are provided in the proximal segment of the supporting loops an in the lens portion to provide grip for pronged tip forceps prior to and during fixation. The configuration of the supporting loops permit a single size of anterior chamber intraocular lens or posterior chamber intraocular lens to fit any eye size.

It is therefore a primary object of the present invention to provide supporting loops for both anterior and posterior chamber intraocular lenses which are sufficiently flexible to accommodate normal imposed compressive forces without any discomfort.

Another object of the present invention is to provide a single sized anterior or posterior chamber intraocular lens which may be used in any sized eye within a large range of eye sizes.

Still another object of the present invention is to provide an anterior and posterior chamber intraocular lens implant which has a maximum width of six millimeters, the diameter of the lens itself.

Yet another object of the present invention is to provide an anterior or posterior intraocular lens implant which has a maximum dimension of 13½ millimeters and which is compressible to a dimension of 11.5 millimeters with no lens bowing anteriorly or posteriorly.

Yet another object of the present invention is to provide anterior and posterior chamber intraocular lens implants which are physically free of the iris and permit normal pupillary movement.

A further object of the present invention is to provide a true posterior chamber intraocular lens with no dependence on the pupillary sphincter and useable after either intracapsular or extracapsular cataract removal.

A still further object of the present invention is to provide a posterior chamber intraocular lens which may be fixated within the anterior chamber peripherally.

A yet further object of the present invention is to provide a posterior chamber intraocular lens which is fixated entirely posterior to the iris and anterior to the remaining lens capsule in an extracapsular eye.

A yet further object of the present invention is to provide a posterior chamber intraocular lens implant which is useable in any sized intracapsular to extracapsular eye.

These and other object of the present invention will become apparent to those skilled in the art as the description thereof proceeds.

The present invention may be described with greater specificity and clarity with respect to the following drawings, in which.

Figure 1:
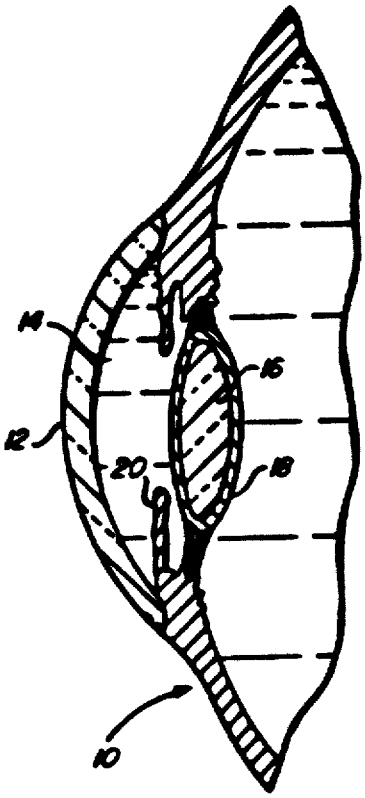
FIG. 1 is a cross-sectional view of a normal eye.

Referring to FIG. 1, a normal eye will be briefly described. Cornea 12 is a clear transparent tissue which acts as a transmissive element for light. It also has some capability for focusing the transmitted light upon the retina (not shown). The light transmitted through the cornea passes through anterior chamber 14 and the fluid disposed therein and impinges upon a crystaline lens 16. The lens acts as a major focusing element for the light penetrating therethrough upon the retina. A fluid known as vitreous humor is a light transmitting medium intermediate the lens and the retina. Lens 16 is encased within a capsule 18. Iris 20 is disposed anterior of lens 16 and serves in the nature of a diaphragm to regulate the amount of light impinging upon the lens.

When cataract occurs, clouded areas form within the lens. These clouded areas affect the transmissivity of light therethrough and impair sight. When the cloud becomes sufficiently severe, the only treatment available is surgical removal of the lens itself. Such removal is referred to as extracapsular cataract surgery (extracapsular eye) when capsule 18 remains either partially or entirely intact within the eye. Removal of the lens together with the supporting capsular tissue or capsule 18 is referred to as intracapsular cataract surgery (intracapsular eye).

Figure 9:
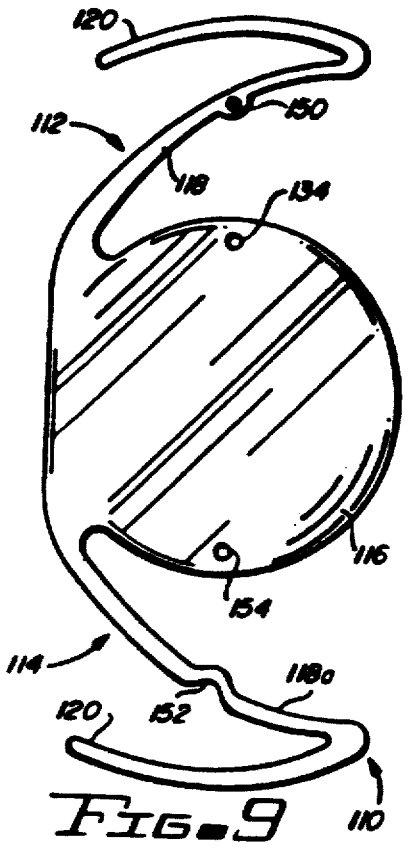
FIG. 9 is a plan view of a posterior chamber intraocular lens implant.
Figure 10:
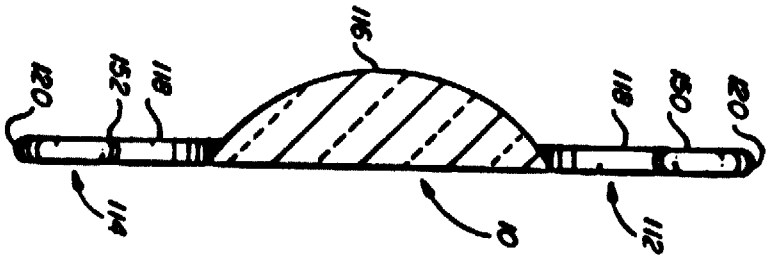
FIG. 10 illustrates a cross-sectional view of a posterior chamber intraocular lens.

FIGS. 2 through 7 illustrate various anterior chamber intraocular lens implants and FIGS. 9 and 10 illustrate a posterior chamber intraocular lens implant, any of which may be used to replace a lens 16 removed by either intracapsular or extracapsular cataract surgery.

Each of these implants includes an optical portion having a plano-convex surface with the convex surface facing anteriorly. Nominally, the optical portion is 6 millimeters in diameter. Supporting loops having a nominal width of 0.25 millimeters extend in generally diametrically opposed directions from the optical portion. These supporting loops and the optical portion may be of one piece construction of separate pieces with the supporting loop firmly inserted into the optical portion at a predetermined angle and orientation. The major dimension across the implant diameter is nominally 13.5 millimeters and the width is no more than that of the lens, 6 millimeters. The material of the implants may be of polymethylmethacrylate or other nonabsorbable nontoxic sterile material.

Figure 2:
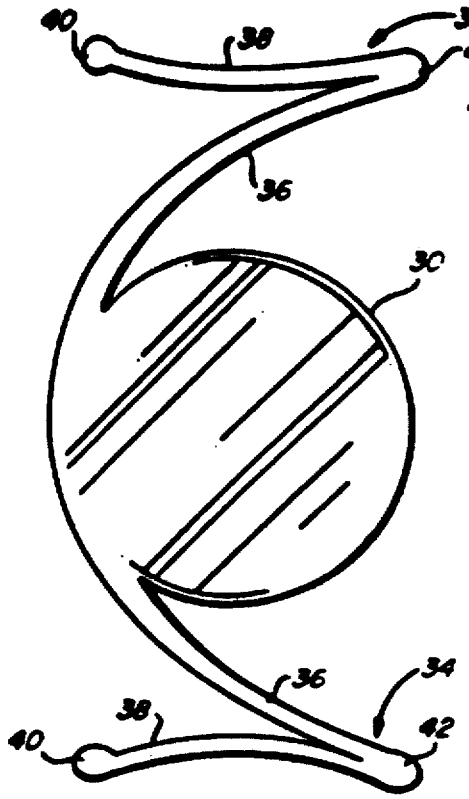
FIGS. 2 to 7 illustrate variously configured anterior chamber intraocular lens implants embodying the principles of the present invention.

Referring to FIG. 2, there is shown a lens portion 30 retained in place by supporting loops 32 and 34. The supporting loops are mirror images of one another in both configuration and size. Each segment 36 is curved and extends from a point essentially tangential to optical portion 30. Segment 38 is curved interiorly toward the optical portion from between fixation points 40 and 42, the latter also being the junction with segment 36. Both fixation points are smoothly rounded to preclude abrading and irritating the point of contact with the eye. By inspection, it will become apparent that any compressive force imposed upon any two points of fixation will result in bending of any intermediate segments and compliance with any such imposed compressive force does not depend upon compression or elongation of a segment along its longitudinal axis.

Figure 3:
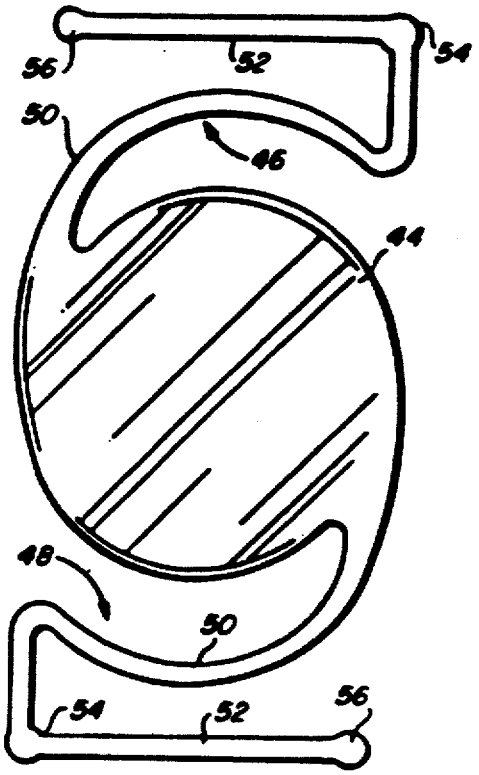

FIG. 3 illustrates a lens portion 44 having supporting loops 46, 48 extending tangentially from diametrically opposed locations on the lens portion. Since the supporting loops are identical but reversely oriented, a description of one will apply to the other. Segment 50 of supporting loop 46 extends tangentially from the edge of lens portion 44 and thereafter curves somewhat concentrically with the lens portion through a substantial arc whereafter it extends exteriorly in general parallel laterally offset relationship with a radial of the lens portion bisecting the curved part of the segment. Segment 52 extends perpendicularly from the extremity of segment 50 for a distance approximately equal with the diameter of the lens portion. The junction between the two segments and the extremity of segment 52 are curved smooth surfaced and define fixation points 54, 56.

By inspection, it will become apparent that any compressive force imposed intermediate the fixation points of supporting loop 46 and 48 will result in bending of two or more of the segments. Moreover, compliance with such compressive force is not dependent upon compression or elongation of any segment along its longitudinal axis. It may be noted that upon application of a compressive force intermediate fixation points of supporting loops 46 and 48, some counter-clockwise rotation of lens 44 may occur. Such rotation has no effect upon the optics of the lens portion and the patient will be unaware of it.

Figure 4:
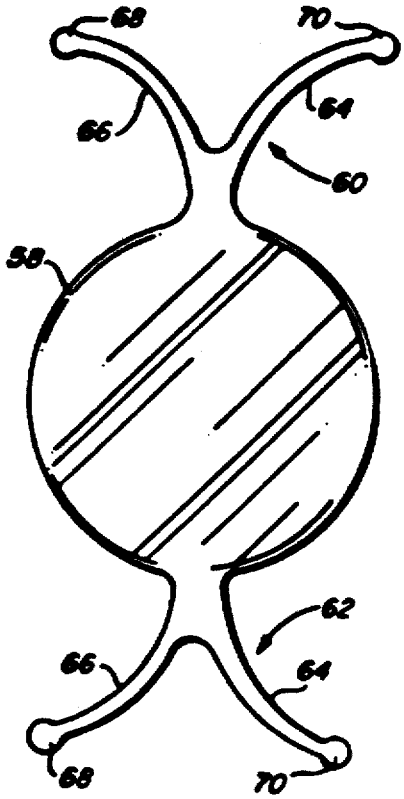

FIG. 4 illustrates a lens portion 58 having diametrically opposed supporting loops, 60, 62. Each supporting loop includes a pair of exteriorly oppositely curved segments 64, 66. The segments are terminated by bulbous ends which serve as fixation points 68, 70, respectively. The configuration of the segments of supporting loops 60 and 62 provide compliance with any compressive force exerted intermediate any two fixation points by bending of the intermediate segments. The overall flexibility of this implant may be somewhat less than that of the implants described above because of the diametrically opposed junctions in combination with the radially centered disengaging orientation of each pair of segments.

Figure 5:
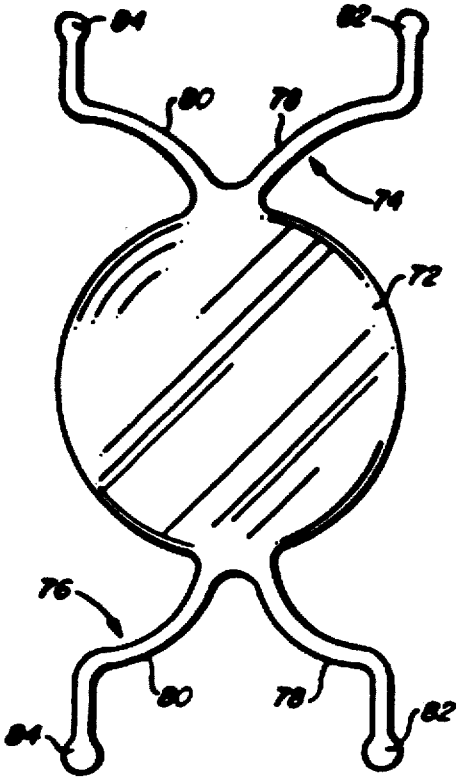

The implant illustrated in FIG. 5 is a direct variant of that shown in FIG. 4. Herein, lens portion 72 includes a pair of diametrically opposed supporting loops 74, 76. Each loop includes segments 78, 80 diverging from a junction. Each segment includes a curved section and a straight section extending from the extremity of the curved section and along a ling parallel to and offset of a radial of the lens portion passing through the junction of the relevant supporting loop. The bulbous end of each straight section of segments 78, 80 serves as a fixation point 82, 84.

Figure 6:
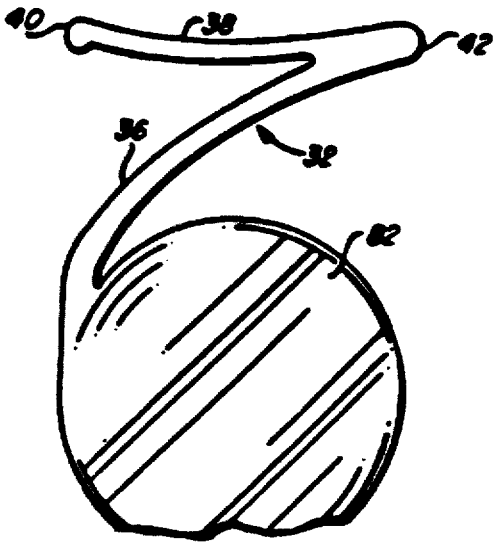

FIG. 6 illustrates an anterior chamber intraocular lens implant which includes a lens portion 82 retained in place by a supporting loop 32 in the type described with respect to FIG. 2. A second supporting loop, located in diametrically opposed relationship thereto may be of the configuration of supporting loop 60 shown in FIG. 4 or supporting loop 74 shown in FIG. 5.

Figure 7:
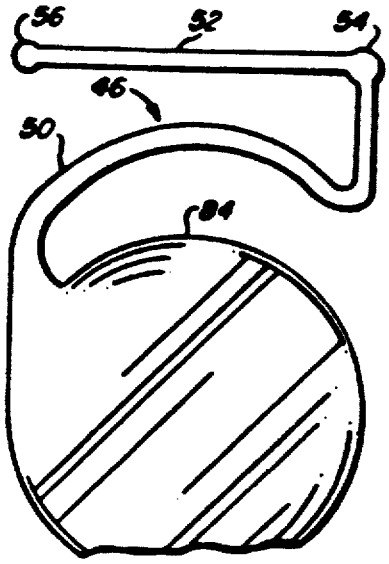

FIG. 7 illustrates an anterior chamber intraocular lens having a lens portion 84 supported by a supporting loop 46 of the type described with respect to FIG. 3. The diametrically oriented opposed supporting loop may be either supporting loop 60 shown in FIG. 4 or supporting loop 74 shown in FIG. 5.

Figure 8:
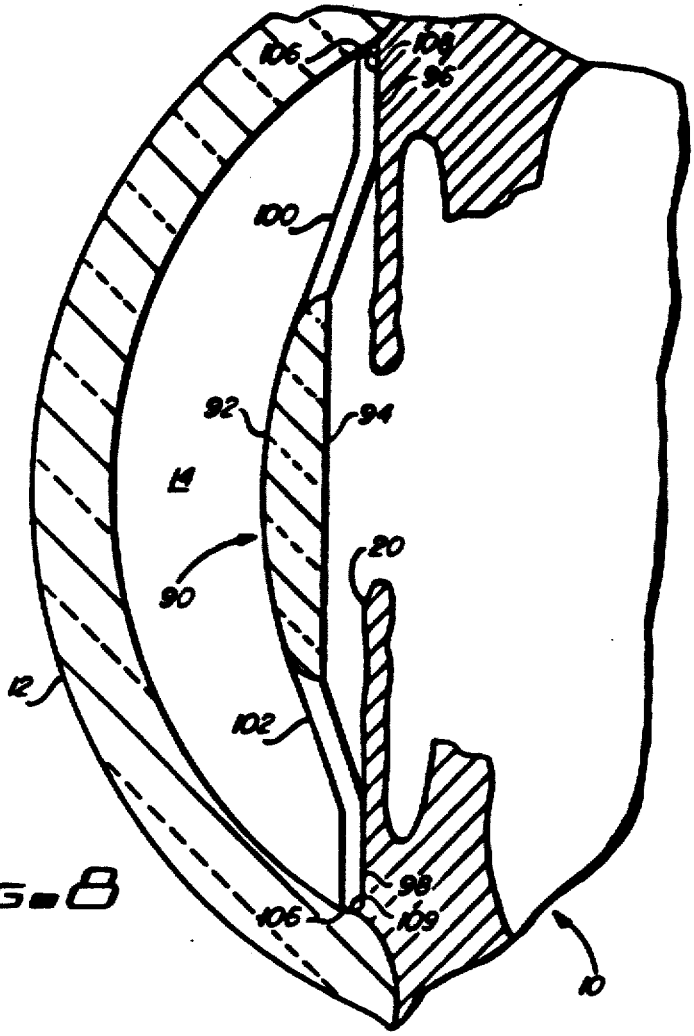
FIG. 8 illustrates a cross-sectional view and implant position of an anterior chamber intraocular lens.

Referring to FIG. 8, there is shown an anterior chamber intraocular lens implant 90 located within eye 10. The selection of implant 90 may be any one of the type illustrated in FIG. 2 through 7, the selection of which is dependent upon various criteria not presently germain. To insure a noncontacting relationship between the implant and iris 20, a vault of approximately 0.5 millimeters is formed between the planoposterior surface 94 of lens portion 92 and posterior surfaces 96, 98 attendant the extremities of supporting loops 100, 102. As illustrated, implant 90 is supported by the fixation points 104, 106 in angles 108, 109 within the anterior chamber. It may be noted that eye 10 is illustrated as having undergone intracapsular cataract surgery although it is to be understood implantation could as easily have been accomplished had the eye undergone extracapsular cataract surgery.

Referring jointly to FIGS. 9 and 10, there is shown a posterior chamber intraocular lens implant 110. The structure of this implant permits implantation within the posterior chamber of any sized eye and irrespective of whether the cataract has been removed by extracapsular or intracapsular surgery. A pair of supporting loops 112, 114, extend tangentially in opposed directions from the perimeter of lens portion 116. In the embodiment illustrated, the supporting loops are mirror images of one another and only one of them will be described in detail. Supporting loop 112 includes a segment 118 which is curved interiorly toward lens portion 116. A further segment 120 extends from the extremity of segment 118 and is folded back upon it; this segment is also curved interiorly toward lens portion 116 and may be concentric therewith. It may be curved as shown to provide an infinite number of fixation points. As particularly illustrated in FIG. 10, supporting loops 112 and 114 may lie in the same plane as the plane of the plano-convex lens portion 116. Alternatively, the supporting loops may be set at an angle of approximately 10° with respect to the posterior plane of the lens portion, as illustrated in FIG. 12.

Figure 11:
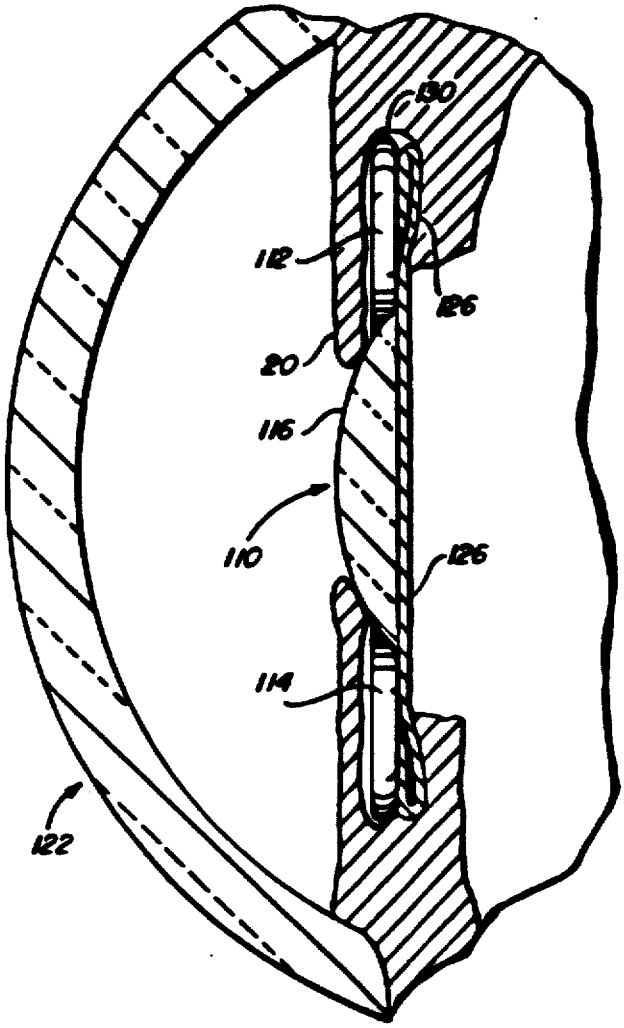
FIG. 11 illustrates the implant position of a posterior chamber intraocular lens in an extracapsular eye.

The fixation of implant 110 in an extracapsular eye is particularly illustrated in FIG. 11. Herein, there is depicted an eye 122 upon which extracapsular surgery has been performed leaving posterior capsule 126. Supporting loops 112, 114, extending from lens 116 of implant 110 are fixated anterior to capsule 126 within a sulcus or groove 130 posterior of iris 20 and at the pupillary periphery; it does not affect pupillary movement.

Figure 12:
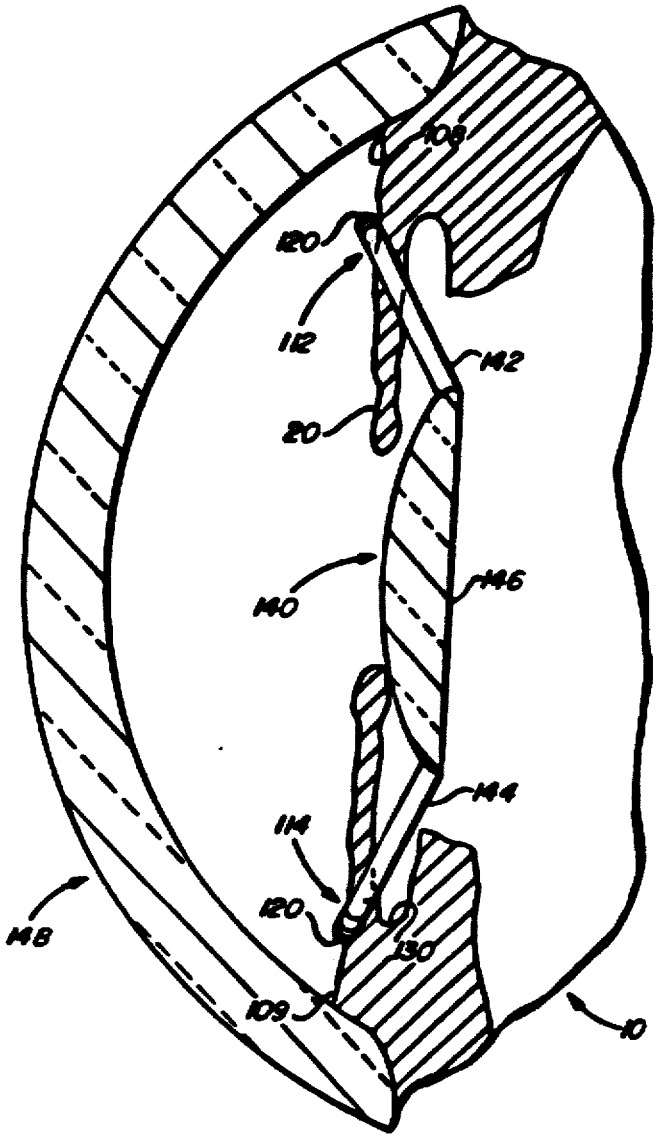
FIG. 12 illustrates the implant position of a posterior chamber intraocular lens in an intracapsular eye.

FIG. 12 illustrates a posterior chamber intraocular lens implant 140 having supporting loops 142, 144 extending in diametrically opposed directions from lens 146. The loops extend forwardly, that is toward the convex surface of the lens, at an angle of approximately 10° with respect to the plane defined by the planar surface of the lens. Implant 140 is shown fixated within an eye 148 which has undergone intracapsular surgery. The segments are either fixated posteriorly with the aid of a non-absorbable fixation suture through iris tissue in the periphery or the segments are manipulated from the posterior chamber to the anterior chamber through a peripheral iridotomy for fixation in the anterior chamber. Segments 120 (see FIG. 9) of supporting loops 142, 144 have been maneuvered from the posterior chamber to the anterior chamber through a peripheral opening of the iris (iridotomy or iridectomy) and fixated in the peripheral portion of the anterior chamber. In either case, the optical portion of the implant remains in the posterior chamber and the points of fixation are at or in proximity to the pupillary periphery to avoid affecting the pupillary movement. It is to be understood that the description above is also applicable to posterior chamber intraocular lens implants in which the supporting loop are not angulated.

As particularly noted in FIG. 9, apertures 150 are disposed in segments 118 of the supporting loops; alternatively, the apertures may be replaced by a radially inwardly oriented depression or groove 152, as shown on segment 118a. These apertures or grooves, in combination with apertures 154 in the lens, are engageable with pronged tips of forceps to permit compressing of the supporting loops to ease manipulation of the implant into the posterior chamber.

While the posterior chamber intraocular lens implant is illustrated in FIGS. 11 and 12 as being generally vertically oriented (note FIG. 9), horizontal orientation is possible Moreover, horizontal orientation for intracapsular eyes positions segments 120 such that penetration through the iris occurs at the ten and two o'clock positions of the eye.

Upon fixation of the posterior chamber intraocular lens implant, essentially all of segments 120 are disposed in the anterior chamber while essentially all of segments 118 are disposed posterior of iris 20 such that the junction between the segments is coincident with the respective peripheral openings in the iris.

A primary advantage of the posterior chamber intraocular lens implant described with particular reference to FIGS. 9 through 12 is that it provides a single sized uniplanar implant that can be used in any sized eye. Furthermore, it retains all of the advantages of a posterior chamber intraocular lens implant and is also suitable for use in an eye which has undergone either extracapsular surgery or intracapsular surgery. Moreover, the disadvantages inherently attendant either anterior chamber intraocular lens implants or iris supported lenses are avoided.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles:

I claim:

1. An intraocular lens implant for intracapsular and extracapsular eyes, said implant comprising in combination:

(a) a lens for focusng the light;

(b) a first supporting loop extending in one direction from said lens, said first supporting loop including at least a first pair of fixation points for supporting said lens within the eye;

(c) a second supporting loop extending in a second direction from said lens and in opposed relationship to said first supporting loop, said second supporting loop including at least a second pair of fixation points for supporting said lens within the eye; and (d) each of said first and second supporting loops including at least one segment for defining at least one of said pair of fixation points, each of said first and second supporting loops including at least a pair of segments, each segment of said pair of segments being generally non-aligned with a radial of said lens and each segment of said pair of segments which extends direction from said lens being oriented generally non-parallel with any ther segment which extends directly from said lens;

whereby, any compressive force applied between two generally opposed ones of said fixation points will result in lateral compression in the plane of the lens rather than anterior or posterior bowing of the affected ones of said segments.

2. The implant as set forth in claim 1 wherein said lens has a diameter of 6 millimeters.

3. The implant as set forth in claim 2 wherein in an uncompressed state the distance between the opposing extremities of said first and second supporting loops is 13.5 millimeters.

4. The implant as set forth in claim 3 wherein upon application of a compressive force, the distance between the opposing extremities of said first and second supporting loops in a compressed state is 11.5 millimeters without causing bowing of said lens.

5. The implant as set forth in claim 4 wherein the width of said implant at any point is no greater than the diameter of said lens.

6. The implant as set forth in claim 1 wherein the width of said implant at any point is no greater than the diameter of said lens.

7. The implant as set forth in claim 6 wherein in an uncompressed state the distance between the opposing extremities of said first and second supporting loops is 13.5 millimeters.

8. An anterior chamber intraocular implant for intracapsular and extracapsular eyes, said implant comprising in combination:

(a) a plano-convex lens for focusing the light;

(b) a first supporting loop extending in a first direction from said lens, said first supporting loop including at least a first pair of fixation points for supporting said lens within the eye;

(c) a second supporting loop extending in a second direction from said lens and in opposed relationship to said first supporting loop, said second supporting loop including at least a second pair of fixation points for supporting said lens within the eye;

(d) each of said first and second supporting loops including at least one segment for defining at least one of said pair of fixation points, each of said first and second supporting loops including at least a pair of segments, each segment of said pair of segments being generally non-aligned with a radial of said lens and each segment of said pair of segments which extends directly from said lens being oriented generally non-parallel with any other segment which extends directly from said lens; and (e) a vault formed by said lens intermediate the extremities of said first and second supporting loops for ensuring a separation between said lens and the iris of the eye on implantation.

9. The implant as set forth in cliam 8 wherein each of said first and second supporting loops comprises: (1) first and second segments extending tangentially in opposed directions from a generally common point on the perimeter of said lens, respectively; and, (2) third and fourth segments extending at an acute angle from the extremities of said first and second segments, respectively.

10. The implant as set forth in claim 9 wherein each of said first and second segments is curved and non-concentric with said lens.

11. The implant as set forth in claim 10 wherein each of said third and fourth segments is curved and generally concentric with said lens.

12. The implant as set forth in claim 11 wherein said first and second pairs of fixation points are formed by the extremities of said third and fourth segments, respectively.

13. The implant as set forth in claim 8 wherein said first and second supporting loops comprise: (1) first and second segments extending tangentially in opposed directions from opposed diametric points of said lens, respectively; and, (2) third and fourth segments extending at an acute angle from the extremities of said first and second segments, respectively.

14. The implant as set forth in claim 13 wherein each of said first and second segments is curved and non-concentric with said lens.

15. The implant as set forth in claim 14 wherein each of said third and fourth segments is curved and generally concentric with said lens.

16. The implant as set forth in claim 15 wherein said first and second pairs of fixation points are formed by the extremities of said third and fourth segments, respectively.

17. The implant as set forth in claim 8 wherein said first and second support loops comprise a first pair of diverging segments extending from the perimeter of said lens and a second pair of diverging segments extending from the perimeter of said lens in a diametrically opposed direction, respectively.

18. The implant as set forth in claim 17 wherein said first and second pairs of fixation points are formed by the extremities of said first and second pairs of said diverging segments, respectively.

19. The implant as set forth in claim 18 wherein said first and second pairs of diverging segments are mirror image of one another.

20. The implant as set forth in claim 19 wherein each said diverging segments is curved toward said lens.

21. The implant as set forth in claim 8 wherein said first supporting loop comprises a first segment extending tangentially from the perimeter of said lens and a second segment extending at an acute angle from the extremity of said first segment, and said second supporting loop comprises a pair of diverging segments extending from the perimeter of said lens in generally diametrically opposed relationship to said first supporting loop, said first pair of fixation points being disposed at the extremities of said second segment and said second pair of fixation points being define by the extremities of said diverging segments.

22. A posterior chamber intraocular implant for intrcapsular and extracapsular eyes, said implant comprising in combination:

(a) a plano-convex lens for focusing the light;

(b) a supporting first loop extending in one direction from said lens, said first supporting loop including first fixation points for supporting said lens within the eye;

(c) a second supporting loop extending in a second direction from said lens and in opposed relationship to said first supporting loop, said second supporting loop including second fixation points for supporting said lens within the eye; and (d) said first and second supporting loops comprising:

(1) first and second segments extending tangentially in opposed directions from a generally common point on the perimeter of said lens, respectively; and (2) third and fourth segments extending at an acute angle from the extremities of said first and second segments, respectively, said first and second segments being generally non-aligned with a radial of said lens and being oriented generally non-parallel with one another.

23. The implant as set forth in claim 22, including means disposed in said first and second supporting loops for manipulating said implant into place.

24. The implant as set forth in claim 23 including further means disposed in said lens for manipulating said implant into place.

25. The implant as set forth in claim 24 wherein said further manipulating means comprises apertures diametrically oriented in said lens.

26. The implant as set forth in claim 25 wherein said manipulating means comprises apertures.

27. The implant as set forth in claim 25 wherein said manipulating means comprises grooves.

28. The implant as set forth in claim 22 wherein each of said first and second segments is curved and non-concentric with said lens.

29. The implant as set forth in claim 28 wherein each of said third and fourth segments is curved and generally concentric with said lens.

30. The implant as set forth in claim 29 wherein said first and second fixation points are formed by the surface of said third and fourth segments, respectively.

31. The implant as set forth in claim 22 wherein a part of each of said first and second supporting loops are set at an angle anteriorly of said lens from the planar posterior surface of said lens.

32. The implant as set forth in claim 31 wherein the angle is 10 degrees.

*33. An intraocular lens suitable for implantation in a human eye comprising:*

*(a) a lens for focusing the light;*

(b) a first supporting loop extending in one direction from said lens, said first supporting loop including at least a first pair of fixation points for supporting said lens within the eye;

(c) a second supporting loop extending in a second direction from said lens and in opposed relationship to said first supporting loop, said second supporting loop including at least a second pair of fixation points for supporting said lens within the eye; and (d) each of said first and second supporting loops including at least one segment for defining at least one of said pair of fixation points, each of said first and second supporting loops including at least a pair of segments, each segment of said pair of segments being generally non-aligned with a radial of said lens and each segment of said pair of segments which extends directly from said lens being oriented generally linearly non-parallel with any other segment which extends directly from said lens;

whereby, any compressive force applied between two generally opposed ones of said fixation points will result in lateral compression in the plate of the lens rather than anterior or posterior bowing of the affected ones of said segments.

34. The intraocular lens as set forth in claim 33 wherein each of said first and second supporting loops comprises: (1) first and second segments extending tangentially in opposed directions from a generally common point on the perimeter of said lens, respectively; and (2) third and fourth segments extending at an acute angle from the extremities of said first and second segments, respectively.

35. The intraocular lens as set forth in claim 33 wherein said first and second supporting loops comprise: (1) first and second segments extending tangentially in opposed diametric points of said lens, respectively; and (2) third and fourth segments extending at an acute angle from the extremities of said first and second segments, respectively.

36. The intraocular lens as set forth in claim 33 wherein said first and second fixation points are formed by the surface of said third and fourth segments, respectively.

37. An intraocular lens suitable for implantation in a human eye comprising:

(a) a lens for focusing the light;

(b) a first supporting loop extending in one direction from said lens, said first supporting loop including at least first fixation points for supporting said lens within the eye;

(c) a second supporting loop extending in a second direction from said lens and in opposed relationship to said first supporting loop, said second supporting loop includes at least second fixation points for supporting said lens within the eye; and (d) each of said first and second supporting loops including at least one segment for defining at least one fixation point of said first and second fixation points, each of said first and second supporting loops including at least a pair of segments, each segment of said pair of segments being generally non-aligned with a radial of said lens and each segment of said pair of segments which extends directly from said lens being oriented generally linearly non-parallel with any other segment which extends directly from said lens;

whereby, any compressive force applied between two generally opposed ones of said fixation points will result in lateral compression in the plane of the lens rather than anterior or posterior bowing of the affected ones of said segments.

38. The intraocular lens as set forth in claim 37 wherein each of said first and second supporting loops comprises: (1) first and second segments extending tangentially in opposed directions from a generally common point on the perimeter of said lens, respectively; and (2) third and fourth segments extending at an acute angle from the extremities of said first and second segments, respectively.

39. The intraocular lens as set forth in claim 37 wherein said first and second supporting loops comprise: (1) first and second segments extending tangentially in opposed diametric points of said lens, respectively; and (2) third and fourth segments extending at an acute angle from the extremities of said first and second segments, respectively.

40. The intraocular lens as set forth in claim 36 wherein said first and second fixation points are formed by the surface of said third and fourth segments, respectively.

41. An anterior chamber intraocular lens for intracapsular and extracapsular eyes, said implant comprising in combination;

(a) a lens for focusing the light;

(b) a first supporting loop extending in a first direction from said lens, said first supporting loop including at least a first pair of fixation points for supporting said lens within the eye;

(c) a second supporting loop extending in a second direction from said lens and in opposed relationship to said first supporting loop, said second supporting loop includes at least a second pair of fixation points for supporting said lens within the eye;

(d) each of said first and second supporting loops including at least one segment for defining at least one of said pair of fixation points, each of said first and second supporting loops including at least a pair of segments, each segment of said pair of segments being generally non-aligned with a radial of said lens and each segment of said pair of segments which extends direction from said lens being oriented generally linearly non-parallel with any other segment which extends directly from said lens; and (e) a vault formed by said lens intermediate the extremities of said first and second supporting loops for ensuring a separation between said lens and the iris of the eye on implantation.

42. The intraocular lens as set forth in claim 41 wherein each of said first and second supporting loops comprises: (1) first and second segments extending tangentially in opposed directions from a generally common point on the perimeter of said lens, respectively; and (2) third and fourth segments extending at an acute angle from the extremities of said first and second segments, respectively.

43. The intraocular lens as set forth in claim 41 wherein said first and second supporting loops comprise: (1) first and second segments extending tangentially in opposed diametric points of said lens, respectively; and (2) third and fourth segments extending at an acute angle from the extremities of said first and second segments, respectively.

44. The intraocular lens as set forth in claim 41 wherein said first and second fixation points are formed by the surface of said third and fourth segments, respectively.

45. An anterior chamber intraocular lens for intracapsular and extracapsular eyes, said implant comprising in combination;

(a) a lens for focusing the light;

(b) a first supporting loop extending in a first direction from said lens, said first supporting loop including at least first fixation points for supporting said lens within the eye;

(c) a second supporting loop extending in a second direction from said lens and in opposed relationship to said first supporting loop, said second supporting loop including at least first fixation points for supporting said lens within the eye;

(d) each of said first and second supporting loops including at least one segment for defining at least one of said fixation points, each of said first and second supporting loops including at least a pair of segments, each segment of said pair of segments being generally non-aligned with a radial of said lens and each segment of said pair of segments which extends directly from said lens being oriented generally linearly non-parallel with any other segment which extends directly from said lens; and (e) a vault formed by said lens intermediate the extremities of said first and second supporting loops for ensuring a separation between said lens and the iris of the eye on implantation.

46. The intraocular lens as set forth in claim 45 wherein each of said first and second supporting loops comprises: (1) first and second segments extending tangentially in opposed directions from a generally common point on the perimeter of said lens, respectively; and (2) third and fourth segments extending at an acute angle from the extremities of said first and second segments, respectively.

47. The intraocular lens as set forth in claim 45 wherein said first and second supporting loops comprise: (1) first and second segments extending tangentially in opposed diametric points of said lens, respectively; and (2) third and fourth segments extending at an acute angle from the extremities of said first and second segments, respectively.

48. The intraocular lens as set forth in claim 45 wherein said first and second fixation points are formed by the surface of said third and fourth segments, respectively.

49. A posterior chamber intraocular lens for intracapsular and extracapsular eyes, said implant comprising in combination:

(a) a lens for focusing the light;

(b) a supporting first loop extending in one direction from said lens, said first supporting loop including first fixation points for supporting said lens within the eye;

(c) a second supporting loop extending in a second direction from said lens and in opposed relationship to said first supporting loop, said second supporting loop including second fixation points for supporting said lens within the eye; and (d) said first and second supporting loops comprising: (1) first and second segments extending tangentially in opposed directions from a generally common point on the perimeter of said lens, respectively; and (2) third and forth segments extending at an acute angle from the extremities of said first and second segments, respectively, said first and second segments being generally non-aligned with a radial of said lens and being oriented generally linearly non-parallel with one another.

50. The intraocular lens as set forth in claim 49 wherein said first and second fixation points are formed by the surface of said third and fourth segments, respectively.

51. A posterior chamber intraocular lens for intracapsular and extracapsular eyes, said implant comprising in combination:

(a) a lens for focusing the light;

(b) a supporting first loop extending in one direction from said lens, said first supporting loop including at least a first pair of fixation points for supporting said lens within the eye;

(c) a second supporting loop extending in a second direction from said lens and in opposed relationship to said first supporting loop, said second supporting loop including at least a second pair of fixation points for supporting said lens within the eye; and (d) said first and second supporting loops comprising: (1) first and second segments extending tangentially in opposed directions from a generally common point on the perimeter of said lens, respectively; and (2) third and fourth segments extending at an acute angle from the extremities of said first and second segments, respectively, said first and second segments being generally non-aligned with a radial of said lens and being oriented generally linearly non-parallel with one another.

52. The intraocular lens as set forth in claim 51 wherein said first and second pairs of fixation points are formed by the surface of said third and fourth segments, respectively.

53. An intraocular lens suitable for use in the anterior chamber or posterior chamber of a human eye, comprising:

(a) a lens body having a peripheral edge portion defining a circle;

(b) said lens body having first and second supporting loops extending from opposite sides of the periphery of said lens body;

(c) each of said first and second supporting loops comprising an arm portion having a base joined in the periphery of said lens body with said arm portion extending from said lens body, an elbow, an elongated seating portion having a first end joined to said arm portion by said elbow and an opposite free end extending in a direction such that said elongated seating portion is outward of said arm portion relative to said lens body;

(d) the two bases of said arm portions of said first and second supporting loops being located on opposite sides of said lens body to allow a first plane coinciding with and passing through the axis of said lens body to pass through said two bases;

(e) said arm portions of said first and second supporting loops extending from said lens body in opposite directions relative to each other;

(f) said two bases of said arm portions being further located on opposite sides of a second plane coinciding with and passing through the axis of said lens body, said second plane also passing through said arm portions and through said elongated seating portions;

(g) each arm portion of each of said supporting loops crossing said second plane from its base and has its elbow including the inside edge of its elbow located on a side of said second plane opposite the side on which its base is located;

(h) said elongated seating portions extending from their elbows respectively in opposite directions relative to each other, (i) the curvature of the elbow of each of said supporting loops being much sharper than the curvature of its seating portion;

(j) each of said supporting loops being relatively small in cross-section and resilient such that its arm portion and elbow may be moved toward said lens body and its elongated seating portion may be moved toward its arm portion and hence toward said lens body.

54. The intraocular lens of claim 53 wherein said first and second supporting loops are of similar shape but asymmetrically arranged relative to said lens body.

55. The intraocular lens of claim 53, wherein:

(a) in a plane perpendicular to the axis of said lens body, each supporting loop is flexible about the junction of its base with the periphery of said lens body, (b) in a plane perpendicular to the axis of said lens body, each supporting loop is flexible at its elbow; and (c) in a plane perpendicular to the axis of said lens body, each supporting loop is flexible along its seating portion.

56. The intraocular lens of claim 53 wherein:

(a) said elbows of said first and second supporting loops are located such that said first plane passing through said two bases does not pass through said elbows.

57. An intraocular lens suitable for use as an artificial lens implant in the anterior chamber or posterior chamber of a human eye, comprising:

(a) a lens body having first and second supporting loops extending from opposite sides of the periphery of said lens body;

(b) each of said first and second supporting loops comprising an arm portion having a base joined to the periphery of said lens body with said arm portion extending from said lens body, an elbow, and an seating portion having a first end joined to said arm portion by said elbow, and an opposite free end, said seating portion being located outward of said arm portion relative to said lens body;

(c) the two bases of said arm portions of said first and second supporting loops being located on opposite sides of said lens body and on opposite sides of a plane coinciding with and passing through the axis of said lens body, said plane also passing through said arm portions and through said seating portions;

(d) each arm portion of each of said supporting loops crosses said plane from its base and has its elbow including the inside edge of its elbow located on a side of said plane opposite the side on which its base is located;

(e) each seating portion of each of said supporting loops extends from its elbow in a direction such that it crosses said plane with its free end located on the side of said plane on which its base is located;

(f) the curvature of the elbow of each of said position fixation members is much sharper than the curvature of its seating portion; and (g) each supporting loop being relatively small in cross section and resilient such that its arm portion may be moved toward said lens body and its seating portion may be moved toward its arm portion and hence toward said lens body.

58. The intraocular lens of claim 57 wherein:

(a) in a plane perpendicular to the axis of said lens body, each supporting loop is flexible about the junction of its base within the periphery of said lens body;

(b) in a plane perpendicular to the axis of said lens body, each supporting loop is flexible at its elbow; and (c) in a plane perpendicular to the axis of said lens body, each supporting loop is flexible along its seating portion.

59. The intraocular lens of claim 57 wherein:

(a) said plane passing through the axis of said lens body passes through about the mid-points of said seating portions between their elbow and their free ends and is defined as a central plane;

(b) the peripheral edge of said lens body on opposite sides of said central plane is tangential to two planes parallel to said central plane;

(c) the elbow of said first supporting loop including its inside edge is closer to one of said two planes than to said central plane;

(d) the elbow of said second supporting loop including its inside edge is closer to the other of said two planes than to said central plane;

(e) the free end of said first supporting loop is closer to said other of said two planes than to said central plane; and (f) the free end of said second supporting loop is closer to said one of said two planes than to said central plane.

60. An intraocular lens suitable for use as an artificial lens in the anterior chamber or posterior chamber of a human eye, comprising:

a) a lens body having first and second supporting loops extending from opposite sides of the periphery of said lens body;

b) each of said first and second supporting loops comprising an arm portion having a base joined to the periphery of said circular lens body with said arm portion extending from said lens body, an elbow, and a seating portion having a first end joined to said arm portion by said elbow, and an opposite free end, said seating portion being located outward of said arm portion relative to said lens body;

c) the two bases of said arm portions of said first and second supporting loops being located on opposite sides of said lens body to allow a first plane coinciding with and passing through the axis of said lens body to pass through said two bases;

d) the two bases of said arm portions of said first and second supporting loops being located on opposite sides of and equally spaced from a second plane coinciding with and passing through the axis of said lens body, said second plane also passing through said arm portions and through said seating portions;

e) said arm portions of said first and second supporting loops extending from said lens body in opposite directions relative to each other;

f) said seating portions extending from their elbows respectively in opposite directions relative to each other;

g) each arm portion of each of said first and second supporting loops crosses said second plane from its base and has its elbow including the inside edge of its elbow located on a side of said second plane opposite the side on which its base is located;

h) each seating portion of each of said first and second supporting loops extending from its elbow in a direction such that it crosses said second plane with its free end located on the side of said second plane on which its base is located; and i) each of said first and second supporting loops being relatively small in cross-section and resilient such that its arm portion and elbow may be moved toward said lens body and its seating portion may be moved toward its arm portion and hence toward said lens body.

61. The intraocular lens of claim 60 wherein the curvature of the elbow of each of said first and second supporting loops is much sharper than the curvature of its seating portion.

62. The intraocular lens of claim 60, wherein:

a) in a plane perpendicular to the axis of said lens body, each of said first and second supporting loops is flexible about the junction of its base with the periphery of said lens body;

b) in a plane perpendicular to the axis of said lens body, each of said first and second supporting loops being flexible at its elbow; and c) in a plane perpendicular to the axis of said lens body, each of said first and second supporting loops being flexible along its seating portion.

63. The intraocular lens of claim 60 wherein:

a) the peripheral edge of said lens body on opposite sides of said second plane being tangential to two planes parallel to said second plane;

b) the elbow of said first supporting loop, including its inside edge, being closer to one of said two planes than to said second plane;

c) the elbow of said second supporting loop, including its inside edge, being closer to the other of said two planes than to said second plane;

d) the free end of said first supporting loop being closer to said other of said two planes than to said second plane; and e) the free end of said second supporting loop being closer to said one of said two planes than to said second plane.

64. The intraocular lens of claim 60 wherein:

a) each of said arm portions includes an inside edge facing a portion of said lens body; and b) the junction of each of said inside edges of each of said arm portions with said lens body being located on the same side of said second plane as its base of said bases.

65. An intraocular lens suitable for use as an artificial lens in the anterior chamber or posterior chamber of a human eye, comprising:

(a) a lens body having first and second supporting loops extending from opposite sides of the periphery of said lens body;

(b) each of said first and second supporting loops comprising an arm portion having a base joined to the periphery of said lens body with said arm portion extending from said lens body, and elbow, and an seating portion having a first end joined to said arm portion by said elbow, and a free end, said seating portion being located outward of said arm portion relative to said lens body;

(c) the two bases of said arm portions of said first and second supporting loops being located on opposite sides of said lens body and on opposite sides of a plane passing through said lens body, through said arm portions and through about the midpoints of said seating portions between their elbows and their free ends;

(d) each arm portion of each of said supporting loops crosses said plane from its base and has its elbow including the inside edge of its elbow located on a side of said plane opposite the side on which its base is located;

(e) each seating portion of each of said supporting loops extends from its elbow in a direction such that it crosses said plane with its free end located on the side of said plane on which its base is located;

(f) the curvature of the elbow of each of said supporting loops is much sharper than the curvature of its seating portion; and (g) each supporting loop being relatively small in cross-section and resilient such that its arm portion may be moved toward said lens body and its elongated seating portion may be moved toward its arm portion and hence toward said lens body.

66. The intraocular lens of claim 65, wherein:

(a) said arm portions of said first and second supporting loops extend from said lens body in opposite directions relative to each other; and (b) said elongated seating portions extend from their elbows respectively in opposite directions relative to each other.

67. An intraocular lens suitable for use as an artificial lens implant in the anterior chamber or posterior chamber of the human eye, comprising:

(a) a lens body having a peripheral edge portion defining a circle;

(b) said lens body having first and second position fixation members extending from opposite sides of the periphery of said lens body;

(c) each of said first and second arm fixation members comprising an arm portion having a base joined to the periphery of said lens body with said arm portion extending from said lens body, an elbow, an elongated outward-convex seating portion having a first end joined to said arm portion by said elbow and an opposite free end extending in a direction such that said elongated outward-convex seating portion is outward of said arm portion relative to said lens body;

(d) the two bases of said arm portions of said first and second portion fixation members being located on opposite sides of said lens body to allow a first plane coinciding with and passing through the axis of said lens body to pass through said two bases;

(e) said arm portions of said first and second position fixation members extending from said lens body in opposite directions relative to each other;

(f) said two bases of said arm portions being further located on opposite sides of a second plane coinciding with and passing through the axis of said lens body, said second plane also passing through said arm portions and through said outward-convex seating portions;

(g) each arm portion of each of said position fixation members crossing said second plane from its base and has its elbow including the inside edge of its elbow located on a side of said second plane opposite the side on which its base is located;

(h) said elongated outward-convex seating portions extending from their elbows respectively in opposite directions relative to each other;

(i) the curvature of the elbow of each of said position fixation members being much sharper than the curvature of its outward-convex seating portion;

(j) the distance between the elbow and the free end of each of said position fixation members being greater than the distance between its outward-convex seating portion and the nearest edge of said lens body;

(k) each position fixation member being relatively small in cross-section and resilient such that its arm portion and elbow may be moved toward said lens body and its elongated outward-convex seating portion may be moved toward its arm portion and hence toward said lens body; and (l) each of said outward-convex seating portions providing a broad area of tissue contact and fixation when said insert is implanted in the eye.

68. An intraocular lens device for implantation into a human eye, said lens device comprising:

(a) an optical lens suitable for replacing a human crystalline lens and being operable to be selectively positioned within either an anterior chamber or a posterior chamber of a human eye;

(b) a first haptic member connected to said optical lens and extending outwardly from said lens and operably, upon insertion of the intraocular lens device within either the anterior or posterior chamber of a human eye, into contact with interior peripheral portions of the eye to at least partially support said optical lens within the eye, said first haptic member comprising;

(i) a first segment projecting on each side of an imaginary plane extending normal to and bisecting said optical lens, (ii) a loop portion extending from one end of said first segment and turning, from an imaginary extension of said first segment away from said imaginary plane, back toward said imaginary plane, (iii) a second segment extending from the other end of said second loop portion and projecting through said imaginary plane and joining a generally peripheral portion of said optical lens on the other side of said imaginary plane with respect to the position of said loop portion of said first haptic member;

(c) a second haptic member connected to said optical lens and extending outwardly from said optical lens and operably, upon implantation of said lens device within an eye, into contact with interior peripheral portions of the eye to cooperate with said first haptic member to fully support said optical lens within the eye, said second haptic member comprising;

(i) a first segment projecting on each side of the imaginary plane extending normal to and bisecting said lens and extending in a posture generally diametrically opposed to said first segment of said first haptic member, (ii) a loop portion extending from one end of said first segment and turning, from an imaginary extension of said first segment away from said imaginary plane, back toward said imaginary plane, said loop portion of said second haptic member being positioned on an opposite said of said imaginary plane with respect to said loop portion of said first haptic member, (iii) a second segment extending from the other end of said loop portion and projecting through said imaginary plane and joining a generally peripheral portion of said optical lens on the other side of said imaginary plane with respect to the position of said loop portion of said second haptic member and said second segment of said second haptic member joining said optical lens in a peripheral posture generally diametrically opposed to the position in which said second segment of said first haptic member joins said optical lens;

(d) said first haptic member and said second haptic member extend outwardly from said optical lens symmetrically upon diametrically opposite sides of said lens and operably flex, upon deflection from first and second haptic members, to promote planar rotation of said optical lens within an eye and concomitantly minimize vaulting movement of said optical lens normal to the plane of said optical lens.

69. An intraocular lens as defined in claim 68 wherein said optical lens, in side view, is elevated with respect to the outermost portions of said first and second haptic members.

70. An intraocular lens as defined in claim 68, wherein:

(a) said second segment of said first haptic member joins a generally peripheral portion of said optical lens in a position rotated approximately ninety degrees around said optical lens with respect to said imaginary plane with respect to said loop portion of said first haptic member; and (b) said second segment of said second haptic member joins a generally peripheral portion of said optical lens in a position rotated approximately ninety degrees around said optical lens on an opposite side of said imaginary plane with respect to said loop portion of said second haptic member and being generally diametrically opposed to the position of joining of said first haptic member.

71. An intraocular lens device for implantation into a human eye, said lens device comprising:

(a) an optical lens suitable for replacing a human crystalline lens and being operable to be selectively positioned within either an anterior chamber or a posterior chamber of a human eye;

(b) a first haptic member connected to said optical lens and extending outwardly from said lens and operably, upon insertion of the intraocular lens device within either the anterior or posterior chamber of a human eye, in contact with interior peripheral portions of the eye to at least partially support said optical lens within the eye, said first haptic member being composed of a flexible rod of polymer material and comprising;

(c) a first arcuate segment having a first free end and a second end said first end extending on one side of a first imaginary plane extending normal to and bisecting said optical lens and said second end extending on the other side of said first imaginary plane;

(d) a loop portion extending from said second end of said first accuate segment and turning from an imaginary extension of said first arcuate segment away from said first imaginary plane, back toward said first imaginary plane;

(e) a second arcuate segment extending from said loop porton and projecting through said first imaginary plane and joining a generally peripheral portion of said optical lens on the other side of first imaginary plane with respect to the position of said loop portion of said first haptic member;

(f) a second haptic member identical with said first haptic member and being connected to said optical lens on the other side of a second imaginary plane bisecting said optical lens and extending normal to said optical lens and said first imaginary plane in a symmetrical position and orientation with respect to said first haptic member; wherein said first and second imaginary planes divide said intraocular lens device into quadrants—which may be designated first, second, third and fourth—in a clockwise direction around a plan view of said optical lens, such that said free end of said first arcuate segment of said first haptic and the position of joining of said second arcuate segment of said first haptic is within the first quadrant and said loop portion of said second haptic being within the second quadrant and the first quadrant and said loop portion of said second haptic being within the second quadrant and the free end of said second arcuate segment of said second haptic and the position of joining of said second arcuate segment of said second haptic being within the third quadrant and said loop portion of said first haptic being within the fourth quadrant, said first haptic member and said second haptic member extended symmetrically upon diametrically opposite sides of said optical lens and operably promote planar rotation of said optical lens and concomitantly minimize vaulting movement of said opti-

*cal lens upon deflection of said first and second haptic members.*

*72. An intraocular lens as defined in claim 71 wherein:*

*(a) said second arcuate segment of said first haptic member joins said optical lens within said first quadrant in a position adjacent to said second imaginary plane; and*

*(b) said second arcuate segment of said second haptic member joins said optical lens within said third quadrant in a position adjacent to the other side of said imaginary plane.*

*73. An intraocular lens as defined in claim 70 wherein:*

*(a) said second arcuate segment of said first haptic member joins said optical lens within said first quadrant in a position adjacent to said second imaginary plane; and*

*(b) said second arcuate of said second haptic member joins said optical lens within said third quadrant in a position adjacent to the other side of said second imaginary plane.*

*74. An intraocular lens device for implantation into a human eye, said lens device comprising:*

*(a) an optical lens suitable for replacing a human crystalline lens and being operable to be selectively positioned within either an anterior chamber or a posterior chamber of a human eye;*

*(b) a first haptic member connected to said optical lens and extending outwardly from said lens and operably, upon insertion of the intraocular lens device within either the anterior or posterior chamber of a human eye, into contact with interior peripheral portions of the eye to at least partially support said optical lens within the eye;*

*(c) a first segment projecting on each side of an imaginary plane extending normal to and bisecting said optical lens;*

*(d) a loop portion extending from one end of said first segment and turning, from an imaginary extension of said first segment away from said imaginary plane, back toward said imaginary plane;*

*(e) a second segment extending from the other end of said loop portion and projecting through said imaginary plane and joining a generally peripheral portion of said optical lens on the other side of said imaginary plane with respect to the positon of said loop portion of said first haptic member;*

*(f) a second haptic member connected to said optical lens and extending outwardly from said optical lens and operably, upon implantation of said lens device within an eye, into contact with interior peripheral portions of the eye to cooperate with said first haptic member to fully support said optical lens within the eye; and*

*(g) wherein at least first haptic member operably flexes upon deflection to promote planar rotation of said optical lens within an eye and concomitantly minimize vaulting movement of said optical lens normal to the plane of said optical lens.*

*75. An intraocular lens implant comprising:*

*(a) a lens for focusing the light;*

*(b) a first supporting loop extending in one direction from said lens, said first supporting loop including at least a first pair of fixation points for supporting said lens within the eye;*

*(c) a second supporting loop extending in a second direction from said lens and in diametrically opposed relationship to said first supporting loop, said second supporting loop including at least a second pair of fixation points for supporting said lens within the eye;*

*(d) said first and second supporting loops including first and second segments comprising at least in part an arcuate section, and third and fourth segments extending in a direction generally opposite to said arcuate section of said first and second segments and carrying said fixation points, respectively; and*

*(e) whereby, any compressive force applied between two generally opposed ones of said fixation points will result in lateral compression in the plane of the lens rather anterior or posterior bowing of the affected ones of said segments.*

*76. An intraocular lens implant according to claim 75 wherein said third and fourth segments are straight.*

*77. An intraocular lens implant according to claim 75 wherein said third and fourth segments are concave.*

*78. An intraocular lens implant according to claim 75 wherein said third and fourth segments are convex.*

*79. An intraocular lens implant according to claim 75 wherein said first and second segment further comprise a straight portion extending directly from said lens body.*

*80. An intraocular lens implant according to claim 75 wherein said first and second segments further comprise a straight portion extending from the arcuate section to said third and fourth segments, respectively.*

*81. An intraocular lens implant according to claims 75, 76, 77, 78, 79, or 80, wherein said first and second segments and said third and fourth segments are symmetrical but oppositely oriented with respect to each other.*

*82. An intraocular lens implant suitable for implantation in a human eye, said lens implant comprising in combination:*

*a) a lens for focusing the light, said lens having an optical axis and a plane normal to the optical axis;*

*b) a first supporting loop extending in one direction from said lens, said first supporting loop including first fixation means for supporting said lens within the eye;*

*c) a second supporting loop extending in a second direction from said lens and in opposed relationship to said first supporting loop, said second supporting loop including second fixation means for supporting said lens within the eye; and*

*d) each of said first and second supporting loops including at least one segment for defining at least one of said first and second fixation means, each of said first and second supporting loops including at least a pair of segments, each of said pair of segments being generally nonaligned with a radial of said lens and each segment of said pair of segmetns which extends directly from said lens being oriented generally non parallel with any other segment which extends directly from said lens;*

*whereby, any compressive force applied between two generally opposed ones of said fixation means will result in lateral bending of at least one of said first and second supporting loops in the plane of the lens and urge rotation of said lens about the optical axis rather than anterior or posterior bowing of said lens implant.*

*83. An intraocular lens implant according to claim 82, wherein each segment of each of said pair of segments which extends directly from said lens is oriented generally linearly non parallel with any other segment which extends directly from said lens.*

*84. An intraocular lens implant comprising in combination:*

*a) a lens for focusing the light, said lens having an optical axis and a plane normal to the optical axis;*

*b) a first supporting loop extending in one direction from said lens, said first supporting loop including first fixation means for supporting said lens with the eye;*

*c) a second supporting loop extending in a second direction from said lens and in diametrically opposed relationship to said first supporting loop, said second supporting loop including second fixation means for supporting said lens within the eye; and*

*d) said first and second supporting loops including first and second segments comprising at least in part an arcuate section, and third and fourth segments extending in a direction generally opposite to said arcuate section of said first and second segments and carrying said first and second fixation means, respectively;*

*whereby, any compressive force applied between two generally opposed ones of said fixation means will result in lateral bending of at least one of said first and second supporting loops in the plane of the lens and urge rotation of said lens about the optical axis rather than anterior or posterior bowing of said lens implant.*

*85. An intraocular lens implant according to claim 84, wherein at least one of said first and second segments comprises a straight section extending directly from said lens.*

*86. An intraocular lens implant according to claim 84, wherein said first and third segments are connected together at an acute angle and said second and fourth segments are connected together at an acute angle.*

* * * * *